United States Patent [19]
Carrington

[11] Patent Number: 6,009,565
[45] Date of Patent: Jan. 4, 2000

[54] PROTECTIVE GARMENT FOR THE HIP AREA

[75] Inventor: Janice Carrington, Worcester, Pa.

[73] Assignee: Plum Enterprises, Valley Forge, Pa.

[21] Appl. No.: 08/744,713

[22] Filed: Oct. 29, 1996

[51] Int. Cl.$^7$ .................................................. A41D 13/00
[52] U.S. Cl. ........................... 2/455; 2/228; 2/238; 2/227
[58] Field of Search ............................... 2/455, 456, 227, 2/228, 238, 22, 23, 69, 267; 602/23, 61

[56] References Cited

U.S. PATENT DOCUMENTS

| | | | |
|---|---|---|---|
| 3,068,871 | 12/1962 | Rapp | 2/227 |
| 4,302,847 | 12/1981 | Miles . | |
| 4,561,123 | 12/1985 | Hull | 2/23 |
| 4,807,301 | 2/1989 | Ferber . | |
| 4,987,613 | 1/1991 | Loverdi et al. | 2/23 |
| 5,052,052 | 10/1991 | Gilford et al. | 2/23 |
| 5,105,473 | 4/1992 | Valtakari | 2/23 |
| 5,365,610 | 11/1994 | Lubahn et al. | 2/227 |
| 5,383,236 | 1/1995 | Sesselmann . | |
| 5,383,920 | 1/1995 | Sikes . | |
| 5,433,355 | 7/1995 | Watkins . | |
| 5,437,618 | 8/1995 | Sikes . | |
| 5,461,730 | 10/1995 | Carrington . | |
| 5,497,511 | 3/1996 | Zade | 2/238 |
| 5,500,952 | 3/1996 | Keyes . | |
| 5,551,082 | 9/1996 | Stewart et al. | 2/228 |
| 5,592,689 | 1/1997 | Matthews | 2/23 |

FOREIGN PATENT DOCUMENTS

| | | | |
|---|---|---|---|
| 3638718 | 8/1987 | Germany | 2/23 |

*Primary Examiner*—Gloria M. Hale
*Attorney, Agent, or Firm*—Seidel, Gonda, Lavorgna & Monaco, PC

[57] ABSTRACT

A protective garment for being disposed against a body to absorb shock and protect selected regions of the body against the shock comprises a protective area for protecting against the shock a region of the body disposed adjacent the protective area and a nonprotective area for providing structural integrity to the garment while providing substantially little protection against the shock to a region of the body disposed against the nonprotective area of the garment. The protective area is adapted to be disposed on the side of the body only adjacent the enarthrodial joint of the hip and to be centered on the side of the body slightly below the level of the acetabulum of the pelvis and to extend upwardly and anteriorly to the front of the body and approximately centered over the acetabulum of the pelvis and to extend posteriorly to the rear of the body to the lower region of the gluteal muscles of the body.

20 Claims, 2 Drawing Sheets

PROTECTIVE GARMENT FOR THE HIP AREA

BACKGROUND OF THE INVENTION

The invention relates to a shock and stress protective garment for the hip area, and more particularly to a protective garment that can be worn comfortably and can disperse forces directed toward the hip area, absorbing such forces in the vulnerable regions of the hip.

There are over 300,000 hip fractures each year in the United States. Additionally, there are many other types of hip joint injuries that result in pain. Complications associated with hip injuries, such as pneumonia, can result in disruption of normal life, substantial medical costs and even death. These fractures and other injuries are particularly common among the elderly, who experience degenerative changes in bone and tissue structure with advancing age. The degenerative changes become much worse after a hip fracture. In view of ever increasing life expectancies, the number of injuries of this type and the costs associated with them can be expected to increase with time.

The hip joint is an enarthrodial or ball-anad-socket joint formed by the reception of the ball-shaped head on the upper or proximal end of the femur into the cup-shaped cavity in the pelvis called the acetabulum. A fall or blow tD the hip bone area, if the area is unprotected, can result in body tissue injuries, dislocation of the femur head from the acetabulum, and fractures of the acetabulum or various parts of the proximal femur or other damage in the vicinity of the hip. Particularly vulnerable is the so-called greater trochanter which protrudes outwardly from the proximal femur just below the joint and the adjoining thin neck of the femur. This region is relatively poorly protected by muscle and other body tissue in comparison with the regions of the hip surrounding it. In fact, the greater trochanter is readily accessible to the touch, its position being generally indicated by an elevation in the hip area due to the thinness of the tissues that cover it.

Prior art garments that are capable of providing a measure of protection with respect to these problems are usually difficult to apply and uncomfortable to wear. An effective hip area shock and stress protective garment that is sufficiently comfortable to wear for extended periods of time under clothing, including during normal daytime activities, as well as while sleeping at night, is not available.

In the prior art, U.S. Pat. No. 4,641,641 discloses an annular pad of resilient material that carries adhesive strips on one surface to secure a pad directly to the skin and a domeshaped shield. U.S. Pat. No. 4,573,216 discloses a pad that protects only small isolated areas, such as the immediate area where the greater trochanter approaches the surface of the body. It depends on adhesive to fix it to the skin. The adhesive taught in this manner is not comfortable for long periods of wear. U.S. Pat. No. 2,889,830 is designed to protect only the area of the greater trochanter. Furthermore, it is bulky in design and uncomfortable because of its hard component parts and straps. The bulky components make it undesirable from a cosmetic perspective. The same is true of U.S. Pat. No. 3,526,221. The protective device taught by U.S. Pat. No. 3,526,221 protects only the area of the greater trochanter and is designed in such a way that it is uncomfortable to wear for extended periods of time. U.S. Pat. Nos. 1,756,358 and 1,774,739 are hard, uncomfortable devices worn under clothing designed primarily for sports. These devices are also undesirable from a cosmetic perspective.

Thus, the prior art patents teach many devices for the protection of the hip area. However, the devices taught in the prior art do not solve the problem of providing an effective, light, comfortable hip protective garment which is cosmetically acceptable.

Accordingly, a primary object of the present invention is to provide a shock and stress protective garment that reduces the likelihood of fracture or other injury of the hip or surrounding area and is cosmetically acceptable.

Another object of the invention is to provide a shock and stress protective garment that can be worn and removed easily without straps, bandages or other devices that are difficult to apply and manipulate, especially by older people with arthritic or weak hands.

Another object of the invention is to provide a shock and stress protective garment for the hip area that is lightweight and comfortable to wear for extended periods of time.

Another object of the invention is to provide a shock and stress protective garment for the hip area that is relatively unobtrusive physically and cosmetically, and is comfortable to wear.

SUMMARY

A protective garment for being disposed against a body to absorb shock and protect selected regions of the body against the shock comprises a protective area for protecting against the shock a region of the body disposed adjacent the protective area and a nonprotective area for providing structural integrity to the garment while providing substantially little protection against the shock to a region of the body disposed against the nonprotective area of the garment. The protective area is adapted to be disposed on the body only adjacent the enarthrodial joint of the hip and to be disposed on the side of the body slightly below the level of the acetabulum of the pelvis and to extend upwardly and anteriorly to the front of the body and to be disposed over the acetabulum of the pelvis and to extend posteriorly to the rear of the body to the lower region of the gluteal muscles of the body.

DETAILED DESCRIPTION OF THE INVENTION

Figure 2:
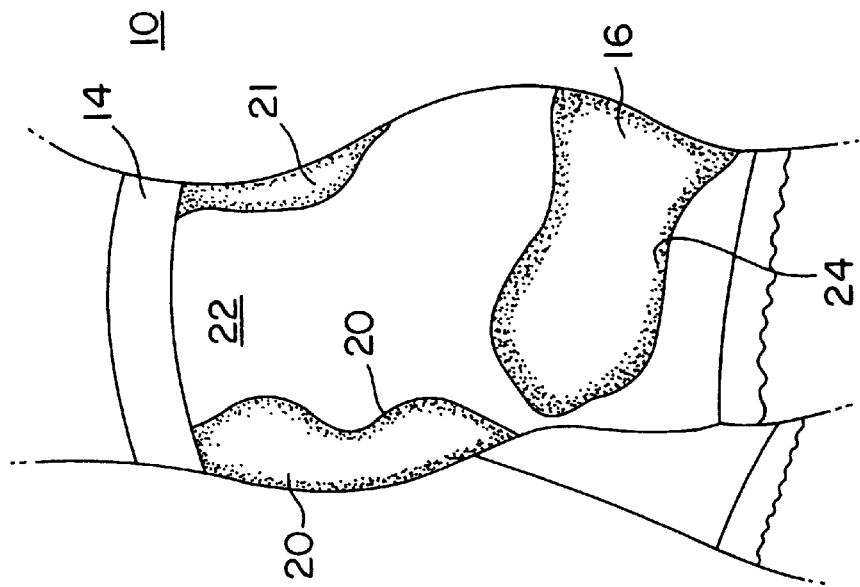
FIG. 2 is a side view of the protective garment of the present invention.
Figure 1:
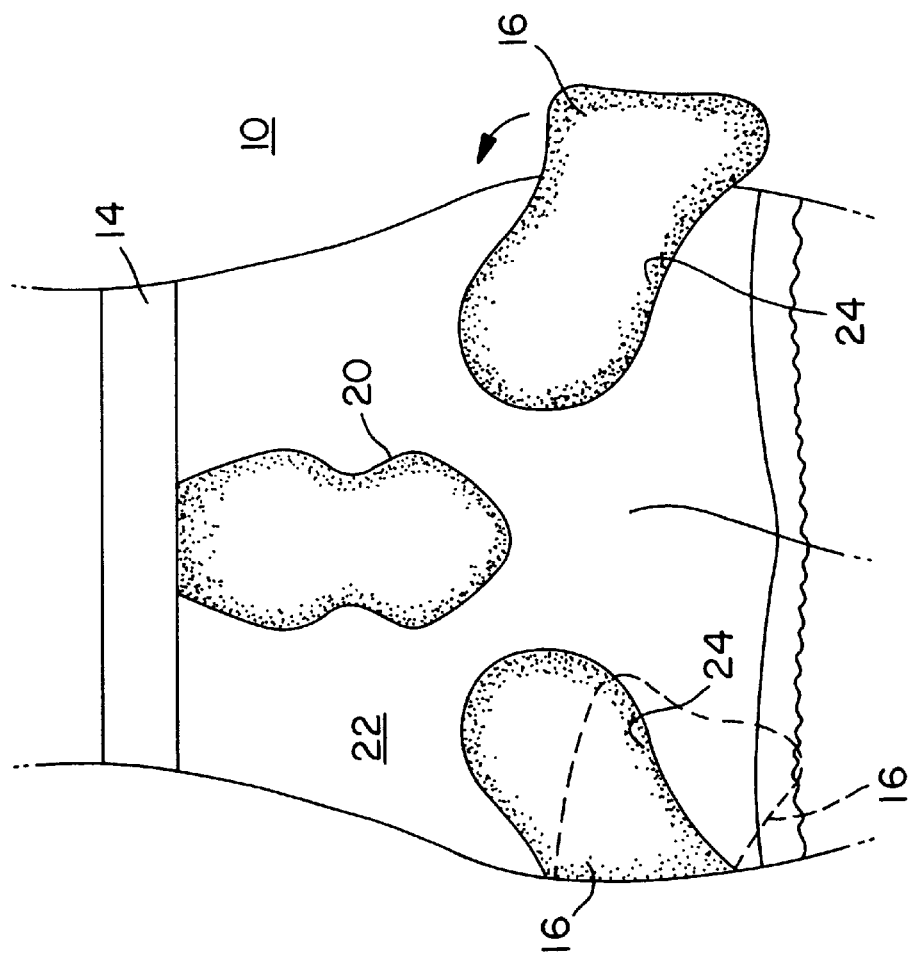
FIG. 1 is a front view of the protective garment of the present invention.

Referring now to FIGS. 1 and 2, there are shown front and side views, respectively, of protective garment 10 of the present invention. Protective garment 10 is a girdle-like garment that can be worn by a user to absorb shocks and stresses to the hip regions of the body and thereby prevent hip fractures and other types of hip injuries that can result from such shocks and stresses. For example, protective garment 10 can be used to prevent hip injuries due to shocks and stresses to the hip regions associated with falls suffered by the user.

Protective garment 10 includes protective areas 16 and nonprotective areas 22. Protective areas 16 of protective garment 10 are disposed adjacent the hip regions of the body of the user for absorbing shocks applied to the hip regions and thereby protecting the hip regions from injury. Nonprotective areas 22 of protective garment 10 can be formed of conventional materials that are associated with conventional girdles for providing structural integrity to protective garment 10, while maintaining protective areas 16 in their desired locations adjacent the vicinity of the hip regions of the user. Nonprotective areas 22 of protective garment 10 can extend from the waist of the user at elastic band 14 to or below the thigh region.

Figure 3:
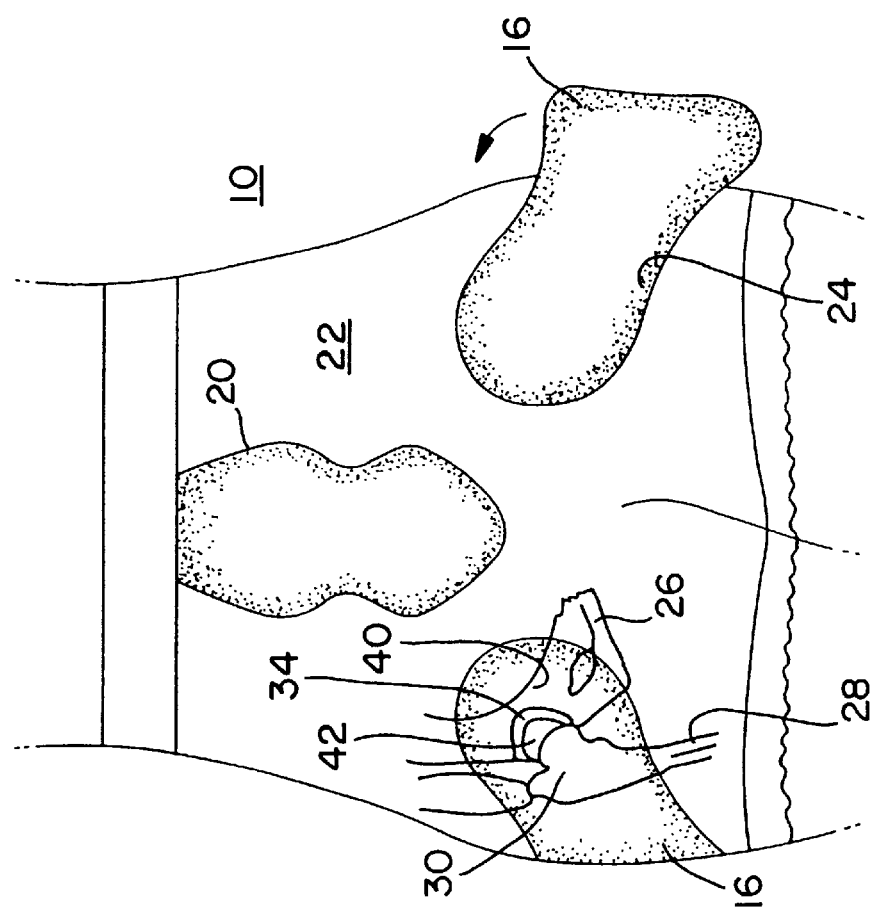
FIG. 3 is a front phantom view of the skeletal anatomy of a user of the protective garment of the present invention.

Referring now to FIG. 3, there is shown a front phantom view of a portion of the skeletal anatomy of a user of protective garment 10 of the present invention. As shown in the drawings, protective regions 16 are disposed adjacent the side of the body of the user of protective garment 10 such that protective regions 16 are approximately centered over an area of femur 28 that is slightly below the neck 30 of femur 28. Thus protective regions 16 are approximately centered slightly below the acetabulum 34 of pelvis 26 on the sides of the user. Protective regions 16 extend from the sides of the user anteriorly and posteriorly around the body of the user in order to partially encircle and protect the regions in the vicinity of ball-and-socket hip joint.

As protective region 16 extends anteriorly around the body of the user it also extends upwardly so that it passes over ball-and-socket joint where the proximal head 42 of femur 28 is received by acetabulum 34 of pelvis 26. In this, manner protective region 16 is approximately centered over acetabulum 34 on the front of the user. Preferably, protective region 16 extends upwardly to a point at least slightly beyond curvature 40 of pelvis 26.

As protective region 16 extends posteriorly from the side of the user, it also extends downwardly. In this manner it is formed to pass along the lower region of the gluteus muscles of the user. In the preferred embodiment of the invention protective region 16 is formed to extend about one-half of the way across the lower region of the buttock of the user.

The size of protective regions 16 varies as needed in order to fit individual users in the manner shown and set forth herein. Thus, there can be a wide range of possible sizes of protective regions 16. In a prototype model of protective garment 10 a protective region 16 of a size acceptable for an individual of normal size had a dimension of approximately 23 cm. at its maximum length and a dimension of approximately 13 cm. at its maximum width. Although this size was believed to be suitable for the prototype, it will be understood that substantially different sizes are required depending on the size of the user. Thus, the size is selected as required to cover the necessary region as previously specified according to the individual user.

It will be understood that regions 16 can be formed substantially larger than as set forth herein with respect to the hip area. However, in order to provide the most comfort for extended periods of wear and to provide the least cosmetic intrusiveness, it is preferred that protective regions 16 be the minimum size consistent with good protection of the user from hip injuries.

Figure 4:
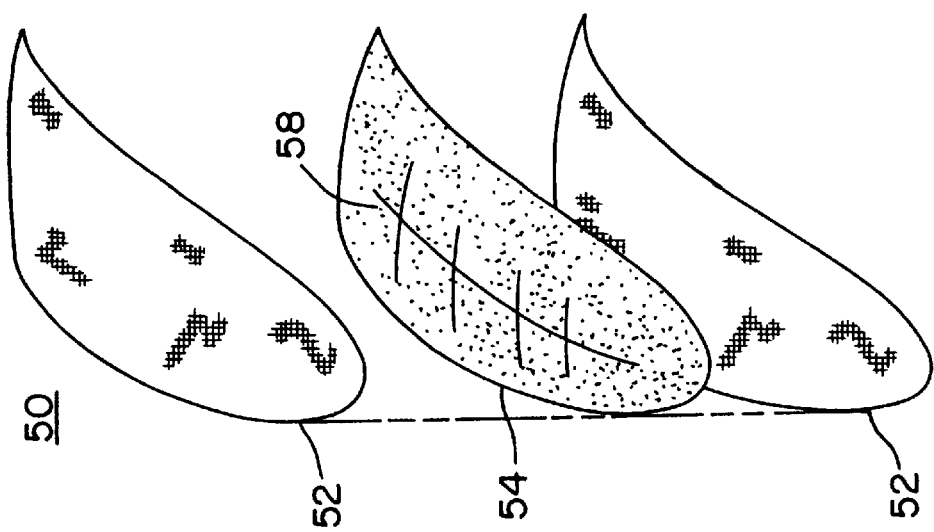
FIG. 4 is an exploded view of a shock absorbing pad suitable for use with the protective garment of the present invention.

Referring now to FIG. 4, there is shown an exploded view of shock absorbing pad 50 which can be used for forming protective areas 16 of protective garment 10 of the present invention. In the preferred embodiment of the invention protective areas 16 can include shock absorbing pads 50 that are formed of shock absorbing core 54 and shell pieces 52 for encapsulating shock absorbing core 54. Shock absorbing core 54, and hence shell pieces 52 with which it is associated, is shaped to be operatively disposed so that it overlies and fully protects the hip of the user as previously described.

In the preferred embodiment of the invention, when shock absorbing core 54 is enclosed by shell pieces 52 shell pieces 52 are stitched together around their peripheries and outside the periphery of core 54. Thus, the size and shape of shell pieces 52 should approximate the size and shape of core 54 with which they are associated. In the preferred embodiment, this shape is substantially as shown in FIGS. 1, 2, 3. Details of the construction and materials of pads suitable for use as shock absorbing pads 50 are set forth in detail in U.S. Pat. No. 5,467,730 issued to Jamie D. Carrington which is incorporated by reference herein.

Shock absorbing pads 50 can be either removably attached to nonprotective areas 22 or fixed to nonprotective areas 22 in order to form protective regions 16. Core 54 of pads 50 is preferably formed of a high density closed cell impact absorbent material such as Ensolite HH. It will be understood that use of a high density foam rather than a relatively lower density foam permits core 54 to be made thinner and more cosmetically acceptable for a desired amount of shock absorption. This is desirable since protective garment 10 is adapted to be worn as an undergarment and it is preferable that it not be detectable. Although closed cell foam is preferred for forming core 54, it is understood that open cell foam can be used in keeping with the spirit of the invention if closed cell foam is desired for a particular reason. Additionally, core 54 can be formed of sponge material. It will also be understood that shock absorbent core 54 can be made of any number of layers of foam wherein the foam layers forming core 54 can have different densities. Shell pieces 52 for encapsulating core 54 can be formed of a cotton knit stretch interlock fabric.

Shock absorbing core 54 can be provided with a plurality of intersecting slits 58. Slits 58 facilitate the conforming of the initially flat core 54 to the compound curvatures of the hip region of the user of protective garment 10. Another advantage provided by slits 58 of core 54 is that slits 58 enhance ventilation thereby making protective garment 10 more comfortable during extended periods of wear by the user.

The material from which the shell pieces 52 are formed can be any suitable fabric. For example, the preferred materials used to form shell pieces 52 can include cotton, nylon, polyester, spandex, elastic and lace. Such materials provide a desirable degree of durability and soil resistance, as well as an acceptable feel and conventional appearance to protective garment 10.

Shock absorbing cores 54 can be formed with a thickness between 1/8 inch and 1 inch if sufficiently dense foam is used. Thicker cores 54 can be beveled for a smoother appearance under the clothing of the user. Cores 54 can be die cut to fit the contour of the hip region as described hereinabove. Additionally, shock absorbing cores 54 can be provided with curvatures 24 in order to prevent pads 50 from restricting the leg movement of the user.

Shock absorbing pads 50 can be sewn into garments or detachably adhered to garments, such as a suitably modified conventional girdle, in order to form protective garment 10 of the present invention. For example, shock absorbing pads 50 can be adhered to such a garment using a book and loop fastener. Velcro Furthermore, the positioning of pads 50 can be customized to the physique of an individual user and to the individual protection requirements of a user using this method of attaching pads 50. For example, multiple pieces of book and loop fastener can be sewn inside the garment in order to permit selective positioning of shock absorbing pads 50 for this purpose.

It will be understood by those skilled in the art that because shock absorbing pads 54 are formed of closed cell foam, they do not absorb water, and that they are therefore substantially waterproof. Thus, it is not necessary to remove them from protective garment 10 when laundering protective garment 10. Additionally, protective garment 10 including pads 50 can, for this reason, be worn under swim wear.

Protective garment 10 can be provided with abdominal support 20 for supporting the abdomen of the user and urging the abdomen of the user inwardly. Abdominal support 20 of protective garment 10 can be formed of a nonwoven interfacing or additional stretch spandex down the center front of protective garme:nt 10 or any other method for providing an inward bias. Protective garment 10 can also be provided with an uplift (not shown) for supporting the gluteus muscles of the user. Additionally, a hidden stretch lock pouch (not shown)can be provided within protective garment 10 in order to hold incontinence pads if needed by the user. Protective garment 10 can also be formed as an all-in-one undergarment (not shown) including a brassier as well as a girdle.

Protective garment 10 can also be provided with lower back support 21. Lower back support 21 of protective garment 10 is effective to stabilize the sacral iliac spine of the user. It can be formed, for example, by providing plastic stays sewn into protective garment 10, by adding further layers of spandex to the material forming the sacral iliac spine region of protective garment 10, or by providing a combination of nylon and neoprene to the region. Any of these methods are effective to provide a small area concealed brace to form a back support 22 within protective garment 10.

The present invention may be embodied in other specific forms without departing from its spirit or essential attributes. Accordingly, reference should be made to the appended claims rather than the foregoing specification and accompanying drawings for an indication of the scope of the invention.

I claim:

1. A protective garment for protecting the enarthrodial joint of a hip of a wearer against shock comprising:
   a protective area comprising a pad;
   a non-protective area providing structural integrity to said garment;
   wherein pad is sized and shaped so as to fully protect said enarthrodial joint from shock applied to the front, side and back of said body;
   said pad comprises at least two layers of material having different densities.

2. The protective garment of claim 1, wherein said protective pad is resilient.

3. The protective garment of claim 1, wherein said protective pad comprises foam material.

4. The protective garment of claim 1, wherein said protective pad is beveled.

5. The protective garment of claim 3, wherein said foam material comprises closed cell foam material.

6. The protective garment of claim 3, wherein said foam material comprises open cell foam material.

7. The protective garment of claim 1, wherein said protective pad has a thickness of between $\frac{1}{8}$ inch and 1 inch.

8. The protective garment of claim 1, wherein said protective pad has a plurality of slits therethrough to provide ventilation.

9. The protective garment of claim 1, said protective pad has a plurality of intersecting slits to provide further ventilation.

10. The protective garment of claim 1, wherein said protective pad is detachably secured to said nonprotective area.

11. The protective garment of claim 1, wherein said protective pad is fixed to said protective area.

12. The protective garment of claim 1, comprising a plurality of protective pads.

13. The protective garment of claim 12, wherein each protective pad of said plurality of protective pads is disposed adjacent an enarthrodial joint region.

14. The protective garment of claim 1, wherein said protective garment comprises a panty girdle.

15. The protective garment of claim 1, further comprising an abdomen support.

16. The protective garment of claim 15, wherein said protective garment has a front and said abdomen support is disposed on the center of the front of said protective garment.

17. The protective garment of claim 15, wherein said abdoen support comprises a non-woven interfacing.

18. The protective garment of claim 15, wherein said abdominal support comprises a stretch material.

19. The protective garment of claim 1, further comprising a gluteal support.

20. The protective garment of claim 1, further comprising a back support panel.

\* \* \* \* \*